United States Patent [19]
Woo et al.

[11] Patent Number: 6,107,290
[45] Date of Patent: Aug. 22, 2000

[54] NON-CRYSTALLINE CEFUROXIME AXETIL SOLID DISPERSANT, PROCESS FOR PREPARING SAME AND COMPOSITION FOR ORAL ADMINISTRATION THEREOF

[75] Inventors: Jong-Soo Woo, Suwon; Hee-Chul Chang, Goyang, both of Rep. of Korea

[73] Assignee: Hammi Pharm Co., Ltd., Kyungki-do, Rep. of Korea

[21] Appl. No.: 09/397,745

[22] Filed: Sep. 16, 1999

[30]     Foreign Application Priority Data

Aug. 4, 1999 [KR] Rep. of Korea ................... 99-31989

[51] Int. Cl.[7] .................................................. A61K 31/545
[52] U.S. Cl. ............................................................. 514/200
[58] Field of Search ............................................. 514/200

[56]         References Cited
         U.S. PATENT DOCUMENTS 4,865,851  9/1989  James et al. ............................. 424/498
4,994,567  2/1991  Crisp et al. .............................. 540/222
5,013,833  5/1991  Crisp et al. .............................. 540/222

*Primary Examiner*—Theodore J. Criares
*Assistant Examiner*—Jennifer Kim
*Attorney, Agent, or Firm*—Anderson Kill & Olick, PC

[57]     ABSTRACT

A non-crystalline cefuroxime axetil solid dispersant showing no absorption peak on a Differential Scanning Calorimetry scan is prepared by (a) dissolving cefuroxime axetil and a surfactant in an organic solvent; (b) suspending a water-insoluble inorganic carrier in the resulting solution; and (c) drying the resulting suspension to remove the organic solvent, said solid dispersant having an improved bioavailability and stability of cefuroxime axetil and being useful for the preparation of a pharmaceutical composition for oral administration.

10 Claims, 1 Drawing Sheet

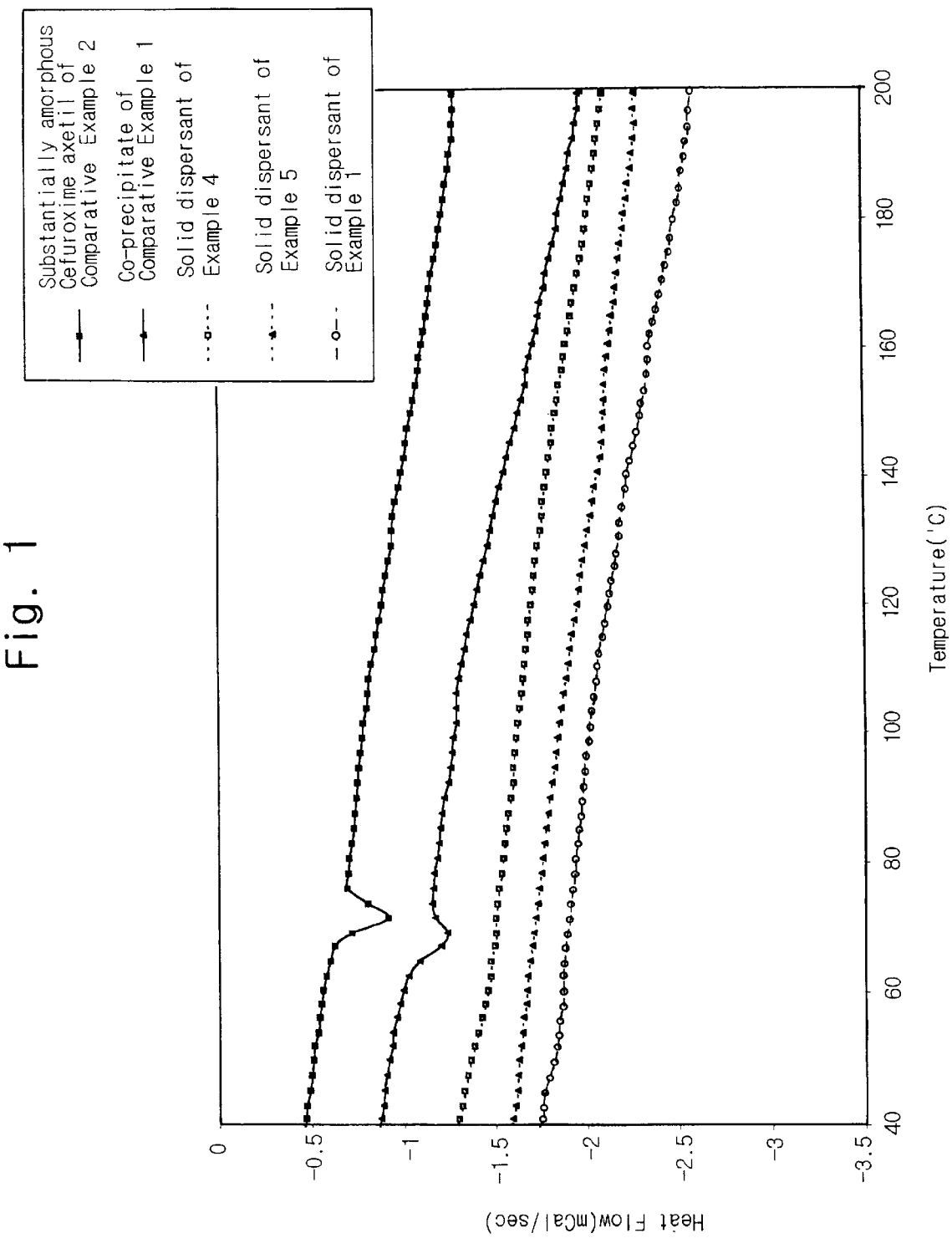

NON-CRYSTALLINE CEFUROXIME AXETIL SOLID DISPERSANT, PROCESS FOR PREPARING SAME AND COMPOSITION FOR ORAL ADMINISTRATION THEREOF

FIELD OF THE INVENTION

The present invention relates to a non-crystalline cefuroxime axetil solid dispersant, a process for preparing same and a composition for oral administration comprising same which has improved cefuroxime axetil bioavailability and stability.

BACKGROUND OF THE INVENTION

Cefuroxime axetil is a cephalosporin antibiotic having a high activity against a wide spectrum of Gram-positive and Gram-negative microorganisms. It shows polymorphism of three forms: a crystalline form having a melting point of about 180° C., a substantially amorphous form having a high melting point of about 135° C. and a substantially amorphous form having a low melting point of about 70° C. The crystalline form of cefuroxime axetil, which is slightly soluble in water and forms a gel upon contact with an aqueous medium, is not readily absorbable in the gastrointestinal tract, rendering its bioavailability on oral administration very low.

U.S. Pat. No. 4,820,833 discloses a process for preparing a highly pure, substantially amorphous form of cefuroxime axetil from the crystalline form, for the purpose of improving the solubility of the drug. The substantially amorphous form of cefuroxime axetil with a low-melting point has a higher water-solubility than the crystalline form. However, it forms a thick gel upon contact with an aqueous medium, thereby causing handling problems in the process for a preparing pharmaceutical composition therefrom. Moreover, the above process is hampered by the problem of a low yield of about 70%, which is caused by the stickiness of the amorphous product.

Further, Korean Patent Publication No. 94-233 teaches a rapidly disintegratable film-coated tablet comprising a core of amorphous cefuroxime axetil and a coating film having a rupture time of less than 40 seconds, which is developed for the purpose of preventing the gelation of cefuroxime axetil in an aqueous medium and also for masking the bitter taste of the drug. This tablet is commercially available as Zinnat® tablet marketed by Glaxo Group Limited (London, England). However, this tablet has a problem in that the bioavailability of cefuroxime axetil may be deteriorated when the rupture time of the coating film is not strictly regulated.

PCT International Publication No. WO 99/08683 discloses a co-precipitate comprising the low-melting point amorphous form of cefuroxime axetil and a water-soluble excipient, e.g., povidone. The co-precipitate is useful for the preparation of a tablet which is not limited by the rupture time of the coating film. However, this co-precipitate undergoes an undesirable property change as it readily absorbs moisture due to the presence of the water-soluble excipient. Further, the co-precipitate, which has high adhesiveness and poor fluidity, is difficult to handle in a spray-drying process and, accordingly, the yield of co-precipitate produced by the disclosed method is low, e.g., about 70%.

Generally, water molecules absorbed by a drug may exist in three forms: weakly adsorbed water on the surface of the drug which is readily evaporizable; water bound to the drug more strongly than the surface water which causes a change in the physicochemical properties, e.g., the melting point, of the drug; and crystal water incorporated in a lattice structure of the drug crystal.

Thermal analysis conducted by the present inventors reveals that the co-precipitate of PCT International Publication No. WO 99/08683 shows a shift in the absorption peak temperature under a moist condition and this shifted peak reverted to the original position under a dry condition. Accordingly, the water adsorbed on the co-precipitate is judged to be bound water which causes a physicochemical change of the drug. Further, despite the use of a water-soluble excipient, the dissolution of cefuroxime axetil from the co-precipitate is not facilitated significantly and, accordingly, the bioavailability of cefuroxime axetil contained in the co-precipitate is relatively low.

The present inventors have endeavored to solve the problems associated with the existing substantially amorphous form of cefuroxime axetil with a low-melting point and succeeded in developing an improved non-crystalline cefuroxime axetil composition having a high stability and bioavailability.

SUMMARY OF THE INVENTION

Accordingly, it is an object of the present invention to provide a non-crystalline cefuroxime axetil solid dispersant having an improved bioavailability and stability.

Another object of the present invention is to provide a process for preparing said dispersant.

A further object of the present invention is to provide a composition for oral administration comprising said dispersant.

In accordance with one aspect of the present invention, there is provided a non-crystalline cefuroxime axetil solid dispersant comprising cefuroxime axetil, a surfactant and a water-insoluble inorganic carrier, said solid dispersant showing no absorption peak on a Differential Scanning Calorimetry scan.

BRIEF DESCRIPTION OF THE DRAWING

The above objects and features of the present invention will become apparent from the following description of preferred embodiments taken in conjunction with FIG. 1 which shows a Differential Scanning Calorimetry (DSC) scan of the non-crystalline cefuroxime axetil solid dispersant of the present invention after 30 day storage under an ambient condition representing no absorption peak.

DETAILED DESCRIPTION OF THE INVENTION

The non-crystalline cefuroxime axetil solid dispersant of the present invention comprises cefuroxime axetil as an active ingredient, a surfactant and a water-insoluble inorganic carrier.

Cefuroxime axetil which may be used in the preparation of the inventive dispersion is any form of cefuroxime axetil, e.g., a crystalline form, low-melting point substantially amorphous form, and high-melting point substantially amorphous form, among which a crystalline form of cefuroxime axetil is preferred.

The surfactant used in the present invention plays a key role in the formation of the non-crystalline solid dispersant of cefuroxime axetil. Representative examples of the surfactant include:

(1) polyoxyethylene-sorbitan-fatty acid esters wherein fatty acid is mono- or tri-lauric, palmitic, stearic or oleic acid (Tween®, ICI), (2) polyoxyethylene glycolated natural or hydrogenated vegetable oils such as polyoxyethylene glycolated natural or hydrogenated castor oil (Cremophor®, BASF),
(3) polyoxyethylene fatty acid esters such as polyoxyethylene stearic acid ester (Myrj, ICI),
(4) polyoxyethylene-polyoxypropylene block copolymer (Poloxamer®, BASF),
(5) sodium dioctyl sulfosuccinate or sodium lauryl sulfate,
(6) phospholipids,
(7) propylene glycol mono- or di-fatty acid esters such as propylene glycol dicaprylate, propylene glycol dilaurate, propylene glycol isostearate, propylene glycol laureate, propylene glycol ricinoleate, propylene glycol caprylic-capric acid diester (Miglyol® 840, H uls),
(8) trans-esterification products of natural vegetable oil triglycerides and polyalkylene polyols (Labrafil® M, Gattefosse),
(9) mono-, di- or mono/di-glycerides such as caprylic/capric acid mono- and di-glycerides (Imwitor®, Gattefosse), and
(10) sorbitan fatty acid esters such as sorbitan monolauryl, sorbitan monopalmityl and sorbitan monostearyl esters (Span®, ICI).

Among those described above, preferred are polyoxyethylene-sorbitan-fatty acid esters, polyoxyethylene-polyoxypropylene block copolymer and a mixture thereof, and more preferred are polyoxyethylene-sorbitan-fatty acid esters.

The water-insoluble inorganic carrier used in the present invention reduces the adhesive property of the cefuroxime axetil dispersant, thereby enhancing the yield thereof in the spray-drying process and also prevents the gelation of cefuroxime axetil when it contacts with an aqueous medium. Representative examples of the water-insoluble inorganic carrier include silicon dioxide, hydrotalcite, aluminum magnesium silicate, aluminum hydroxide, titanium dioxide, talc, aluminum silicate, magnesium aluminum metasilicate, bentonite and a mixture thereof, among which silicon dioxide is preferred.

The solid dispersant of the present invention comprise 1 to 50 parts by weight, preferably 2 to 30 parts by weight, of a surfactant; and 1 to 200 parts by weight, preferably 3 to 50 parts by weight, of a water-insoluble inorganic carrier, based on 100 parts by weight of cefuroxime axetil.

In addition to the cefuroxime axetil, surfactant and water-insoluble inorganic carrier, the solid dispersant of the present invention may further comprise a water-insoluble additive. Representative examples of the water-insoluble additive include microcrystalline cellulose, cross-linked povidone (cross-linked polyvinylpyrrolidone), cross-linked sodium carboxymethylcellulose and a mixture thereof, among which cross-linked sodium carboxymethylcellulose is preferred. The water-insoluble additive may be used in an amount of 100 parts by weight or less, preferably 50 parts by weight or less, based on 100 parts by weight of cefuroxime axetil.

The solid dispersant of the present invention has an enhanced water-solubility and high bioavailability of cefuroxime axetil. Further, cefuroxime axetil in the solid dispersant of the present invention is thermodynamically stable even under a moist condition and resists gelation upon contact with an aqueous medium, due to its interaction with the water-insoluble inorganic carrier.

The solid dispersant of the present invention may be prepared by (a) dissolving cefuroxime axetil and a surfactant in a suitable organic solvent which may be an alcohol (such as methanol and ethanol), acetonitrile, tetrahydrofuran, dichloromethane, chloroform or a mixture thereof; (b) suspending a water-insoluble inorganic carrier in the resulting solution; and (c) drying the resulting suspension to remove the organic solvent in accordance with a conventional method, e.g., spray drying, freeze drying, and evaporation under a reduced pressure. A water-insoluble additive may be further suspended in the solution obtained in (a) before drying.

The inventive process gives the solid dispersant of the present invention in a high yield of 90% or more owing to the reduced adhesiveness and good fluidity of the dispersant.

The solid dispersant of the present invention may be orally administered. Therefore, the pharmaceutical composition of the present invention comprises the non-crystallin cefuroxime axetil solid dispersant in combination with a pharmaceutically acceptable carrier. The pharmaceutical composition may be formulated into various pharmaceutical preparations for oral administration, e.g., in the form of a powder, granule, tablet and coated preparation, in accordance with any of the conventional procedure. For instance, a hard capsule may be prepared by adding pharmaceutical additives to the inventive cefuroxime axetil solid dispersant, processing the mixture to a powder or granules and filling the powder or granules into a hard gelatin capsule; a tablet, by adding a suitable additive to the cefuroxime axetil solid dispersant and tableting the mixture; a coated preparation, by coating a tablet of the inventive dispersant with a film composition in accordance with a conventional coating method. A therapeutically effective amount of cefuroxime axetil may range from 250 mg to 1,000 mg per 1 kg of body weight, as is well known in the art.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Preparation of Solid Dispersant 100 parts by weight of crystalline cefuroxime axetil and 16.63 parts by weight of Tween 80® (ICI) were dissolved in acetone and 16.63 parts by weight of silicon dioxide (surface area: 200±25 $m^2/g$; and particle size: 30 $\mu$m or less) was dispersed therein. The dispersant was subjected to a spray drying using a spray dryer (Minispray dryer B-191, Büchi, Switzerland) at an inlet temperature of 45° C. and outlet temperature of 37° C. to obtain a solid dispersant. The solid dispersant was further dried at 30 to 40° C. for about 3 hours to remove residual solvent.

EXAMPLE 2

Preparation of Solid Dispersant

The procedure of Example 1 was repeated except that 3.33 parts by weight of Tween 800 and 9.98 parts by weight of silicon dioxide were used, to obtain a dried solid dispersant.

EXAMPLE 3

Preparation of Solid Dispersant

The procedure of Example 1 was repeated except that 4.99 parts by weight of Tween 80® and 13.30 parts by weight of silicon dioxide were used, to obtain a dried solid dispersant.

EXAMPLE 4

Preparation of Solid Dispersant 100 parts by weight of crystalline cefuroxime axetil and 6.65 parts by weight of Tween 80® (ICI) were dissolved in acetone and 9.98 parts by weight of cross-linked sodium carboxymethylcellulose and 26.60 parts by weight of silicon dioxide were dispersed therein. The dispersant was subjected to a spray drying using spray dryer (Minispray dryer B-191, Büchi, Switzerland) at an inlet temperature of 45° C. and outlet temperature of 37° C. to obtain a solid dispersant. The solid dispersant was further dried at 30 to 40° C. for about 3 hours to remove residual solvent.

EXAMPLE 5

Preparation of Solid Dispersant

The procedure of Example 4 was repeated except that 16.65 parts by weight of Poloxamer® (BASF) was used in place of Tween 80® to obtain a dried solid dispersant.

COMPARATIVE EXAMPLE 1

Preparation of Co-precipitate 100 parts by weight of crystalline cefuroxime axetil and 9.98 parts by weight of povidone were dissolved in acetone and the solution was subjected to spray drying using a spray dryer (Minispray dryer B-191, Büchi, Switzerland) at an inlet temperature of 45° C. and outlet temperature of 37° C. to obtain a co-precipitate. The co-precipitate was dried at 30 to 40° C. for about 3 hours to remove residual solvent.

COMPARATIVE EXAMPLE 2

Preparation of Substantially Amorphous Cefuroxime Axetil

Crystalline cefuroxime axetil was dissolved to a concentration of 10%(w/v) in acetone and the resulting solution was subjected to spray drying to obtain low-melting point substantially amorphous cefuroxime axetil.

TEST EXAMPLE 1

Thermodynamic Stability Test

Solid dispersant prepared in Examples 1, 4 and 5, the co-precipitate prepared in Comparative Example 1, and the low-melting point substantially amorphous cefuroxime axetil prepared in Comparative Example 2 were stored for 30 days under three storage conditions; ambient condition, 40° C. at 75% relative humidity, and drying condition at 50° C., while monitoring their heat-absorption peaks using a thermoanalysis instrument, Differential Scanning Calorimetry (DSC, Rheometric Scientific DSC plus, England).

FIG. 1 shows DSC scans of the above composition taken at 30 day, and the melting temperature (absorption peak temperature) before and after the 30 days storage are shown in Table I.

TABLE I

| | Initial Peak Temp. (° C.) | Peak Temp. (° C.) after 30 day storage | | |
|---|---|---|---|---|
| | | Ambient Condition | 40° C./ 75% Relative Humidity | 50° C./Dry |
| Solid Dispersant of Example 1 | no peak | no peak | no peak | no peak |
| Solid Dispersant of Example 4 | no peak | no peak | no peak | no peak |
| Solid Dispersant of Example 5 | no peak | no peak | no peak | no peak |
| Co-precipitate of Comparative Example 1 | 69 | 69 | 61 | 75 |

TABLE I-continued

| | Initial Peak Temp. (° C.) | Peak Temp. (° C.) after 30 day storage | | |
|---|---|---|---|---|
| | | Ambient Condition | 40° C./ 75% Relative Humidity | 50° C./Dry |
| Substantially Amorphous Cefuroxime Axetil of Comparative Example 2 | 74 | 74 | 64 | 82 |

As can be seen from FIG. 1 and Table I, the solid dispersants of the present invention show no absorption peak under all storage conditions, which suggests that the inventive dispersants contain stable, non-crystalline cefuroxime axetil. In contrast, both the co-precipitate prepared in Comparative Example 1 and low-melting substantially amorphous cefuroxime axetil prepared in Comparative Example 2 show distinct absorption peaks which shift to a higher temperature region during the 50° C. storage and to lower temperature region during the 40° C. high humidity condition. This observation suggests that both the co-precipitate and low-melting substantially amorphous cefuroxime axetil become more crystalline at 50° C. while their physicochemical properties change by absorbing water at the high humidity condition.

EXAMPLE 6

Preparation of Film-coated Tablet

| Ingredients | Amounts (mg/tablet) |
|---|---|
| Solid Dispersant | |
| Solid dispersant obtained in Example 1 | 400.72 (250 mg as cefuroxime) |
| Pharmaceutical Excipients | |
| Microcrystalline cellulose | 50 |
| Cross-linked povidone | 110 |
| Magnesium stearate | 5 |
| Ingredients of Coated film* | |
| Hydroxypropylmethyl cellulose 2910 (15 cps) | 8 |
| Hydroxypropyl cellulose (10 cps) | 1.34 |
| Ethyl cellulose (10 cps) | 1.34 |
| Concentrated glycerin | 0.69 |
| Talc | 0.07 |
| Titanium dioxide | 0.42 |

*Suspended in a mixture of 260 mg of methylene chloride and 108 mg of ethanol to prepare a coating solution.

Specifically, one half each of the prescribed amounts of microcrystalline cellulose and cross-linked povidone was added to the solid dispersant obtained in Example 1 and the resulting mixture was compressed. Magnesium stearate and the remaining amounts of the excipients were added thereto. The resulting mixture was recompressed with a tablet press into tablets. Subsequently, the prescribed film was coated on the surface of the tablets using the coating solution in a conventional manner.

EXAMPLE 7

Preparation of Tablet

| Ingredients | Amounts (mg/tablet) |
|---|---|
| Solid Dispersant | |
| Solid dispersant obtained in Example 2 | 340.72 (250 mg as cefuroxime) |
| Pharmaceutical Excipients | |
| Microcrystalline cellulose | 50 |
| Cross-linked povidone | 150 |
| Magnesium stearate | 5 |

The procedure of Example 6 was repreated using the above ingredients to prepare tablets.

EXAMPLE 8

Preparation of Hard Capsule

| Ingredients | Amounts (mg/tablet) |
|---|---|
| Solid Dispersant | |
| Solid dispersant obtained in Example 3 | 355.72 (250 mg as cefuroxime) |
| Pharmaceutical Excipients | |
| Microcrystalline cellulose | 20 |
| Cross-linked povidone | 50 |
| Magnesium stearate | 5 |

The pharmaceutical excipients were added to the solid dispersant obtained in Example 3 and the resulting mixture was filled in hard capsules.

EXAMPLE 9

Preparation of Film-coated Tablet

| Ingredients | Amounts (mg/tablet) |
|---|---|
| Solid Dispersant | |
| Solid dispersant obtained in Example 4 | 430.72 (250 mg as cefuroxime) |
| Pharmaceutical Excipients | |
| Cross-linked, sodium carboxymethylcellulose | 40 |
| Microcrystalline cellulose | 50 |
| Cross-linked povidone | 50 |
| Magnesium stearate | 5 |
| Ingredients of Coated film* | |
| Hydroxypropylmethyl cellulose 2910 (15 cps) | 8 |
| Hydroxypropyl cellulose (10 cps) | 1.34 |
| Ethyl cellulose (10 cps) | 1.34 |
| Concentrated glycerin | 0.69 |
| Talc | 0.07 |
| Titanium dioxide | 0.42 |

*Suspended in a mixture of 260 mg of methylene chloride and 108 mg of ethanol to prepare a coating solution.

The procedure of Example 6 was repeated using the above ingredients to prepare film-coated tablets.

EXAMPLE 10

Preparation of Film-coated Tablet

| Ingredients | Amounts (mg/tablet) |
|---|---|
| Solid Dispersant | |
| Solid dispersant obtained in Example 5 | 460.72 (250 mg as cefuroxime) |
| Pharmaceutical Excipients | |
| Cross-linked, sodium carboxymethylcellulose | 40 |
| Microcrystalline cellulose | 50 |
| Cross-linked povidone | 50 |
| Magnesium stearate | 5 |
| Ingredients of Coated film* | |
| Hydroxypropylmethyl cellulose 2910 (15 cps) | 8 |
| Hydroxypropyl cellulose (10 cps) | 1.34 |
| Ethyl cellulose (10 cps) | 1.34 |
| Concentrated glycerin | 0.69 |
| Talc | 0.07 |
| Titanium dioxide | 0.42 |

*Suspended in a mixture of 260 mg of methylene chloride and 108 mg of ethanol to prepare a coating solution.

The procedure of Example 6 was repeated using the above ingredients to prepare film-coated tablets.

COMPARATIVE EXAMPLE 3

| Ingredients | Amounts (mg/tablet) |
|---|---|
| Co-precipitates | |
| Co-precipitates obtained in Comparative Example 1 | 330.72 (250 mg as cefuroxime) |
| Pharmaceutical Excipients | |
| Cross-linked, sodium carboxymethylcellulose | 40 |
| Microcrystalline cellulose | 50 |
| Cross-linked povidone | 50 |
| Magnesium stearate | 5 |
| Ingredients of Coated film* | |
| Hydroxypropylmethyl cellulose 2910 (15 cps) | 8 |
| Hydroxypropyl cellulose (10 cps) | 1.34 |
| Ethyl cellulose (10 cps) | 1.34 |
| Concentrated glycerin | 0.69 |
| Talc | 0.07 |
| Titanium dioxide | 0.42 |

*Suspended in a mixture of 260 mg of methylene chloride and 108 mg of ethanol to prepare a coating solution.

The procedure of Example 6 was repeated using the above ingredients to prepare film-coated tablets.

TEST EXAMPLE 2

Dissolution Test

Dissolution rates of cefuroxime axetil were determined for the film-coated tablets prepared in Examples 6, 9 and 10, and Comparative Example 3 as well as Zinnat® (Glaxo Group Limited, England) as a control, in accordance with the dissolution test method described in the cefuroxime axetil tablet chapter of United States Pharmacopoeia under the conditions listed below:

Test apparatus: Erweka DT80(Erweka, Germany)
Test solution:
  900 ml of 0.07 N HCl
Temperature of test solutions: 37±0.5° C.
Rotation speed: 55±4 rpm Analytical method: liquid chromatography
   column: Cosmosil $C_{18}$(150 mm×4.6 mm; Nacalai Tecque, Japan)
   mobile phase: 0.2M ammonium monophosphate:methanol=620:380
   injection volume: 10 μl
   flow rate: 1.2 ml/min.
   detector: UV 278 nm The ratio of cefuroxime axetil isomers (R and S) released from each film-coated tablet as well as the rupture time of the coating film were determined.

Results are shown in Table II.

TABLE II

| Film-coated Tablet | Ex. 6 | Ex. 9 | Ex. 10 | Comp. Ex. 3 | Control |
|---|---|---|---|---|---|
| Dissolved amount (%) at 15 min. | 84.2 | 81.5 | 86.1 | 64.0 | 84.7 |
| Dissolved amount (%) at 45 min. | 97.1 | 96.7 | 97.6 | 84.0 | 98.0 |
| Ratio of Isomers | 0.50:0.50 | 0.50:0.50 | 0.50:0.50 | 0.50:0.50 | 0.49:0.51 |
| Rupture Time | 1 min. | 1 min. | 1 min. | 1 min. | less than 10 sec |

As can be seen from Table II, the film-coated tablets composition of the present invention containing cefuroxime axetil show dissolution rate comparable to the Zinnat® control in spite of their much improved rupture time of 1 min or more. In contrast, the comparative preparation containing the co-precipitate of cefuroxime axetil and povidone exhibits an inferior dissolution rate. Therefore, the composition of the present invention showing a good dissolution rate are characterized by excellent bioavailability of cefuroxime axetil, that is not limited by the rupture time of the coating film.

What is claimed is:

1. A non-crystalline cefuroxime axetil solid dispersant comprising cefuroxime axetil, a surfactant and a water-insoluble inorganic carrier, said solid dispersant showing no absorption peak on a Differential Scanning Calorimetry scan.

2. The non-crystalline cefuroxime axetil solid dispersant of claim 1, which comprises 1 to 50 parts by weight of a surfactant and 1 to 200 parts by weight of a water-insoluble inorganic carrier based on 100 parts by weight of cefuroxime axetil.

3. The non-crystalline cefuroxime axetil solid dispersant of claim 1, wherein the surfactant is polyoxyethylene-polyoxypropylene block copolymer, polyoxyethylene-sorbitan-fatty acid ester or a mixture thereof.

4. The non-crystalline cefuroxime axetil solid dispersant of claim 1, wherein the water-insoluble inorganic carrier is silicon dioxide.

5. The non-crystalline cefuroxime axetil solid dispersant of claim 1 which further comprises a water-insoluble additive.

6. The non-crystalline cefuroxime axetil solid dispersant of claim 5, wherein the water-insoluble additive is microcrystalline cellulose, cross-linked povidone, cross-linked sodium carboxymethylcellulose or a mixture thereof.

7. The solid dispersant of claim 5, wherein the amount of the water-insoluble additive is 100 parts by weight or less based on 100 parts by weight of cefuroxime axetil.

8. A process for preparing the non-crystalline cefuroxime axetil solid dispersant of claim 1, which comprises (a) dissolving cefuroxime axetil and a surfactant in an organic solvent; (b) suspending a water-insoluble inorganic carrier in the resulting solution; and (c) drying the resulting suspension to remove the organic solvent.

9. The process of claim 8, wherein a water-insoluble additive is further suspended in the solution obtained in (a).

10. A composition for oral administration comprising the non-crystalline cefuroxime axetil solid dispersant of claim 1 or 5 and a pharmaceutically acceptable carrier.

* * * * *